United States Patent [19]

Kohsaka et al.

[11] Patent Number: 4,522,942
[45] Date of Patent: Jun. 11, 1985

[54] PHOSPHORAMIDOTHIONATES

[75] Inventors: Hideo Kohsaka, Hyogo; Sasaki Mitsuru, Osaka; Yukio Ishiguri, Hyogo, all of Japan

[73] Assignee: Sumitomo Chemical Company, Limited, Osaka, Japan

[21] Appl. No.: 500,435

[22] Filed: Jun. 2, 1983

[30] Foreign Application Priority Data

Jun. 3, 1982 [JP] Japan ................................. 57-95764
Nov. 2, 1982 [JP] Japan ............................... 57-192841
Nov. 5, 1982 [JP] Japan ............................... 57-195035

[51] Int. Cl.³ ......................... A01N 57/32; C07F 9/24
[52] U.S. Cl. ..................................... 514/95; 260/940; 260/948; 260/951; 514/100; 549/5; 549/6; 549/218; 549/220
[58] Field of Search ..................... 260/940, 948, 951; 549/5, 6, 218, 220, 268; 424/202, 203, 210, 216, 217

[56] References Cited

U.S. PATENT DOCUMENTS

| | | | |
|---|---|---|---|
| 3,787,538 | 1/1974 | Schrader et al. | 260/951 X |
| 3,792,132 | 2/1974 | Bernhart | 549/220 X |
| 3,822,328 | 7/1974 | Kishino et al. | 260/951 X |
| 3,936,433 | 2/1976 | Satomi et al. | 260/954 |
| 3,943,203 | 3/1976 | Satomi et al. | 260/954 |
| 3,989,502 | 11/1976 | Nishiyama et al. | 71/78 |
| 4,123,526 | 10/1978 | Large | 549/220 X |

FOREIGN PATENT DOCUMENTS 294072 12/1966 Australia.
48-44436 6/1973 Japan.
183743 11/1966 U.S.S.R.

Primary Examiner—Richard L. Raymond
Attorney, Agent, or Firm—Birch, Stewart, Kolasch & Birch

[57] ABSTRACT

A compound of the formula:

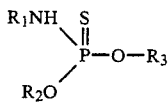

wherein $R_1$ is a hydrogen atom, a lower alkyl group, a lower alkenyl group, a lower alkynyl group, a lower cycloalkyl group, a lower cycloalkyl(lower)alkyl group, a halo(lower)alkyl group, a lower alkoxy(lower)alkyl group, a di(lower)alkoxy(lower)alkyl group, a cyano(lower)alkyl group, a lower alkylthio(lower)alkyl group, a lower alkynylthio(lower)alkyl group, a lower dioxothiacycloalkyl group, a lower thiacycloalkyl group, a lower oxacycloalkyl group, a lower oxacycloalkyl(lower)alkyl group or a thienyl(lower)alkyl group, $R_2$ is a lower alkyl group and $R_3$ is a 3,5-dimethoxyphenyl group, a 3,4-methylenedioxyphenyl group or a 4,5-methylenedioxy-2-nitrophenyl group, which is useful as a fungicide.

24 Claims, No Drawings

PHOSPHORAMIDOTHIONATES

The present invention relates to phosphoramidothionates, and their production and use.

The said phosphoramidothionates are representable by the formula:

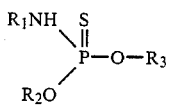

$$\begin{array}{c} R_1NH \\ \diagdown \\ R_2O \end{array} \begin{array}{c} S \\ \| \\ P-O-R_3 \end{array} \qquad (I)$$

wherein $R_1$ is a hydrogen atom, a lower alkyl group, a lower alkenyl group, a lower alkynyl group, a lower cycloalkyl group, a lower cycloalkyl(lower)alkyl group, a halo(lower)alkyl group, a lower alkoxy(lower)alkyl group, a di(lower)alkoxy(lower)alkyl group, a cyano(lower)alkyl group, a lower alkylthio(lower)alkyl group, a lower alkynylthio(lower)alkyl group, a lower dioxothiacycloalkyl group, a lower thiacycloalkyl group, a lower oxacycloalkyl group, a lower oxacycloalkyl(lower)alkyl group or a thienyl(lower)alkyl group, $R_2$ is a lower alkyl group and $R_3$ is a 3,5-dimethoxyphenyl group, a 3,4-methylenedioxyphenyl group or a 4,5-methylenedioxy-2-nitrophenyl group.

In the above significances, the term "lower" is intended to have not more than 8 carbon atoms, and the term "halo" is intended to mean chlorine, bromine, fluorine and iodine, inclusively. Preferred $R_1$ is a hydrogen atom, a $C_1$–$C_5$ alkyl group, a $C_3$–$C_4$ alkenyl group, a $C_3$ alkynyl group, a $C_3$–$C_6$ cycloalkyl group, a $C_3$ cycloalkyl($C_2$)alkyl group, a halo($C_2$–$C_3$)alkyl group, a $C_1$–$C_2$ alkoxy($C_2$–$C_4$)alkyl group, a di($C_1$–$C_2$)alkoxy($C_2$–$C_3$)alkyl group, a cyano($C_1$–$C_3$)alkyl group, a $C_1$ alkylthio($C_3$)alkyl group, a $C_3$ alkynylthio($C_2$)alkyl group, a 1,1-dioxotetrahydrothien-3-yl group, a tetrahydrothiopyran-4-yl group, a tetrahydropyran-4-yl group, a tetrahydrofurfuryl group, a tetrahydrofuryl group, a tetrahydrothienyl group or a 1-(thienyl)ethyl group, and preferred $R_2$ is a $C_1$–$C_2$ alkyl group.

The phosphoramidothionates (I) exhibit not only a preventive effect but also a curative effect against plant diseases such as late blight and downy mildew caused by infection of phytopathogenic fungi belonging to Phycomycetes. They also exhibit a systemic effect against above mentioned plant diseases. Thus, they are useful as fungicides.

Examples of phytopathogenic fungi belonging to Phycomycetes, against which the phosphoramidothionates (I) can exert their fungicidal activity, are as follows: *Peronospora brassicae* on vegetables and radish, *Peronospora spinaciae* on spinach, *Peronospora tabacina* on tobacco, *Pseudoperonospora cubensis* on cucumber, *Plasmopara viticola* on grape, *Plasmopara nivea* on Umbelliferae plants, *Phytophthora cactorum* on apple, strawberry and carrot, *Phytophthora capsici* on tomato and cucumber, *Phytophthora cinnamomi* on pineapple, *Phytophthora infestans* on potato, tomato and eggplant, *Phytophthora nicotianae* var. *nicotianae* on tobacco, kidney bean and onion, *Pythium aphanidermatum* on cucumber, Phythium sp. on spinach, Pythium sp. on wheat, *Phthium debaryanum* on tobacco, Pythium rot (i.e., *P. aphanidermatum, P. debaryanum, P. irregulare, P. myriotylum, P. ultimum*) on soybean and so forth.

Accordingly, the phosphoramidothionates (I) can be used as active ingredients in fungicidal compositions which can be applied to plowed fields, orchards, tea-field, mulberry-field, meadow, lawn and so on.

The phosphoramidothionates (I) may be produced by the reaction of a phosphoramidochloridothionate of the formula:

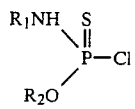

$$\begin{array}{c} R_1NH \\ \diagdown \\ R_2O \end{array} \begin{array}{c} S \\ \| \\ P-Cl \end{array} \qquad (II)$$

wherein $R_1$ and $R_2$ are each as defined above with a 0.9–1.1 mole of a phenol of the formula:

$$R_3OH \qquad (III)$$

wherein $R_3$ is as defined above in a solvent in the presence of a 0.9–1.1 mole of a hydrogen halide removing agent per 1 mole of the phosphoramidochloridothionate (II) at a temperature of 20° to 120° C. for a period of 1 to 5 hours, or by the reaction of a phosphorochloridothionate of the formula:

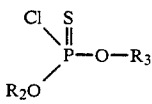

$$\begin{array}{c} Cl \\ \diagdown \\ R_2O \end{array} \begin{array}{c} S \\ \| \\ P-O-R_3 \end{array} \qquad (IV)$$

wherein $R_2$ and $R_3$ are each as defined above with a 1.0–1.2 mole of an amine of the formula:

$$R_1NH_2 \qquad (V)$$

wherein $R_1$ is as defined above in a solvent in the presence of a 1.0–2.2 mole of a hydrogen halide removing agent per 1 mole of the phosphorochloridothionate (IV) at a temperature of 0° to 50° C. for a period of 1 to 5 hours.

Examples of the solvent are an aromatic hydrocarbon (e.g. benzene, toluene, xylene), a halogenated hydrocarbon (e.g. chloroform, carbon tetrachloride, dichloroethane, chlorobenzene, dichlorobenzene), an ether (e.g. diethyl ether, diisopropyl ether, dioxane, tetrahydrofuran, diethyleneglycol dimethyl ether), a ketone (e.g. acetone, methylethylketone, cyclohexanone), a nitro compound (e.g. nitroethane, nitrobenzene), a nitrile (e.g. acetonitrile), a tertiary amine (e.g. pyridine, triethylamine, N,N-diethylaniline, tributylamine, N-methylmorpholine), an acid amide (e.g. N,N-dimethylformamide, N,N-dimethylacetamide), water and a mixture thereof.

Examples of the hydrogen halide removing agent are an organic base (e.g. pyridine, triethylamine, N,N-diethylaniline) and an inorganic base (e.g. sodium hydroxide, potassium hydroxide, sodium carbonate, potassium carbonate).

After completion of the reaction, the reaction product may be isolated by an ordinary separation procedure and, if necessary, purified by a conventional purification procedure such as chromatography, distillation or recrystallization.

Some typical examples of the production of the phosphoramidothionates (I) are shown in the following Examples.

EXAMPLE 1

To a stirred solution of 4,5-methylenedioxy-2-nitrophenol (1.83 g, 10 mmol) in acetonitrile (30 ml) was added anhydrous potassium carbonate (1.40 g, 10 mmol). The mixture was kept at 40°–50° C. for 30 minutes. O-Methyl N-1-(methoxymethyl)propyl phosphoramidochloridothionate (2.32 g, 10 mmol) was added dropwise thereto and refluxed for 3 hours to complete the reaction. Then, the reaction mixture was filtered, and the filtrate was evaporated under reduced pressure. The residue was dissolved in toluene (50 ml), and the solution was washed with an aqueous solution of sodium hydroxide, diluted hydrochloric acid and water and dried over magnesium sulfate. Toluene was evaporated to give an oil which was subjected to chromatography on silica gel to give O-methyl O-4,5-methylenedioxy-2-nitrophenyl N-1-(methoxymethyl)propyl phosphoramidothionate (Compound No. 31) (2.30 g). Yield, 60.8%. $n_D^{25}$ 1.5505.

EXAMPLE 2

To a toluene solution (50 ml) containing O-ethyl O-4,5-methylenedioxy-2-nitrophenyl phosphorchloridothionate (3.23 g, 10 mmol) were added 1-(methoxymethyl)ethylamine (0.89 g, 10 mmol) and triethylamine (1.1 g, 10 mmol), successively, at 0° C. in 40 minutes. The mixture was stirred at room temperature for an additional 3 hours. After completion of the reaction, the resultant mixture was washed with diluted hydrochloric acid and water. The solution was dried over magnesium sulfate, and toluene was evaporated to give O-ethyl O-4,5-methylenedioxy-2-nitrophenyl N-1-(methoxymethyl)ethyl phosphoramidothionate (Compound No. 22) (4.11 g). Yield, 91.1%. $n_D^{27.5}$ 1.5590.

EXAMPLE 3

To a stirred solution of 3,5-dimethoxyphenol (1.54 g, 10 mmol) in acetonitrile (40 ml) was added anhydrous potassium carbonate (1.40 g, 10 mmol). The mixture was kept at 40°–50° C. for 30 minutes. O-methyl N-isopropyl phosphoramidochloridothionate (1.88 g, 10 mmol) was added dropwise thereto in 1 hour and the resultant mixture was refluxed for 3 hours. After completion of the reaction, the solution was filtered and the filtrate was evaporated under reduced pressure. The residue was dissolved in toluene (50 ml). The toluene solution was washed with an aqueous solution of sodium hydroxide, diluted hydrochloric acid and water and dried over magnesium sulfate. Toluene was evaporated to give an oil which was subjected to column chromatography on silica gel. Evaporation of the solvent gave O-methyl O-3,5-dimethoxyphenyl N-isopropyl phosphoramidothionate (Compound No. 66) (1.80 g). Yield, 59.1%. $n_D^{19.5}$ 1.5359.

EXAMPLE 4

To a toluene solution (50 ml) containing O-ethyl O-3,5-dimethoxyphenyl phosphorchloridothionate (2.49 g, 10 mmol) were added 2-(1-cyano)propylamine (0.84 g, 10 mmol) and triethylamine (1.1 g, 10 mmol) successively at 0° C. in 1 hour. The mixture was stirred at room temperature for a further 3 hours. After completion of the reaction, the resultant mixture was washed with diluted hydrochloric acid and water. The toluene solution was dried over magnesium sulfate and evaporated to give O-ethyl O-3,5-dimethoxyphenyl N-2-(1-cyano)propyl phosphoramidothionate (Compound No. 75) (2.75 g). Yield, 92.9%. $n_D^{24.5}$ 1.5368.

EXAMPLE 5

3,4-Methylenedioxyphenol (1.38 g, 10 mmol) and O-ethyl N-isopropyl phosphoramidochloridothionate (2.0 g, 10 mmol) were dissolved in acetonitrile (50 ml). Anhydrous potassium carbonate (1.38 g, 10 mmol) was added thereto, and the mixture was refluxed for 4 hours to complete the reaction. Then, the resultant mixture was filtered and the filtrate was evaporated to given an oil, which was dissolved in toluene (50 ml). The solution was washed with an aqueous solution of sodium hydroxide, diluted hydrochloric acid and water, and dried over magnesium sulfate. Evaporation of toluene gave O-ethyl O-3,4-methylenedioxyphenyl N-isopropyl phosphoramidothionate (Compound No. 81) (2.21 g). Yield, 72.9%. $n_D^{20.0}$ 1.5381.

Examples of the phosphoramidothionate (I) produced in a similar manner are shown in Table 1.

TABLE 1

$$\begin{array}{c} R_1NH \quad S \\ \diagdown \| \\ P-O-R_3 \\ \diagup \\ R_2O \end{array} \quad (I)$$

| Compound No. | $R_1$ | $R_2$ | $R_3$ | Physical constant |
|---|---|---|---|---|
| 1 | sec-$C_4H_9$ | $C_2H_5$ | $O_2N$-phenyl-O-CH$_2$-O (4,5-methylenedioxy-2-nitrophenyl) | M.P. 46–49° C. |
| 2 | iso-$C_3H_7$ | $C_2H_5$ | $O_2N$-phenyl-O-CH$_2$-O | M.P. 85–87° C. |
| 3 | $C_2H_5$ | $C_2H_5$ | $O_2N$-phenyl-O-CH$_2$-O | M.P. 87–90° C. |
| 4 | n-$C_4H_9$ | $C_2H_5$ | $O_2N$-phenyl-O-CH$_2$-O | $n_D^{25.5}$ 1.5361 |
| 5 | $CH_3$ | $C_2H_5$ | $O_2N$-phenyl-O-CH$_2$-O | M.P. 66–70° C. |
| 6 | n-$C_3H_7$ | $C_2H_5$ | $O_2N$-phenyl-O-CH$_2$-O | $n_D^{24.5}$ 1.5572 |

TABLE 1-continued

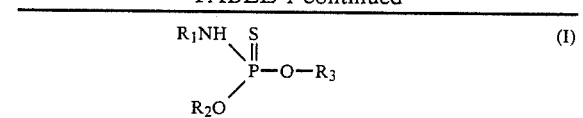

| Compound No. | $R_1$ | $R_2$ | $R_3$ | Physical constant |
|---|---|---|---|---|
| 7 | iso-$C_4H_9$ | $C_2H_5$ | $O_2N$-(3,4-methylenedioxyphenyl) | $n_D^{24.5}$ 1.5532 |
| 8 | $(CH_3)_2CHCH(CH_3)$ | $C_2H_5$ | $O_2N$-(3,4-methylenedioxyphenyl) | $n_D^{24.5}$ 1.5500 |
| 9 | $(C_2H_5)_2CH$ | $C_2H_5$ | $O_2N$-(3,4-methylenedioxyphenyl) | M.P. 84–86° C. |
| 10 | $CH_2=CHCH_2$ | $C_2H_5$ | $O_2N$-(3,4-methylenedioxyphenyl) | $n_D^{24.5}$ 1.5708 |
| 11 | sec-$C_4H_9$ | $CH_3$ | $O_2N$-(3,4-methylenedioxyphenyl) | $n_D^{24.5}$ 1.5610 |
| 12 | iso-$C_4H_9$ | $CH_3$ | $O_2N$-(3,4-methylenedioxyphenyl) | M.P. 90–93° C. |
| 13 | $C_2H_5$ | $CH_3$ | $O_2N$-(3,4-methylenedioxyphenyl) | $n_D^{24.5}$ 1.5580 |
| 14 | H | $C_2H_5$ | $O_2N$-(3,4-methylenedioxyphenyl) | $n_D^{24}$ 1.5700 |

TABLE 1-continued

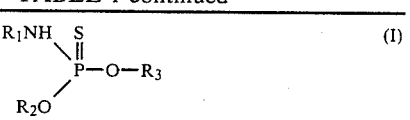

| Compound No. | $R_1$ | $R_2$ | $R_3$ | Physical constant |
|---|---|---|---|---|
| 15 | $CH_3$ | $CH_3$ | $O_2N$-(3,4-methylenedioxyphenyl) | M.P. 63–65° C. |
| 16 | cyclopropyl (H) | $C_2H_5$ | $O_2N$-(3,4-methylenedioxyphenyl) | $n_D^{24.5}$ 1.5770 |
| 17 | $CH_2=C(CH_3)CH_2$ | $C_2H_5$ | $O_2N$-(3,4-methylenedioxyphenyl) | $n_D^{24.5}$ 1.5639 |
| 18 | $HC\equiv CCH_2$ | $C_2H_5$ | $O_2N$-(3,4-methylenedioxyphenyl) | $n_D^{24.5}$ 1.5809 |
| 19 | cyclopentyl (H) | $C_2H_5$ | $O_2N$-(3,4-methylenedioxyphenyl) | M.P. 73–75° C. |
| 20 | cyclobutyl (H) | $C_2H_5$ | $O_2N$-(3,4-methylenedioxyphenyl) | M.P. 77–79° C. |
| 21 | n-$C_3H_7$ | $CH_3$ | $O_2N$-(3,4-methylenedioxyphenyl) | $n_D^{24.5}$ 1.5687 |
| 22 | $CH_3OCH_2CH(CH_3)$ | $C_2H_5$ | $O_2N$-(3,4-methylenedioxyphenyl) | $n_D^{27.5}$ 1.5590 |

TABLE 1-continued $$R_1NH-\underset{\underset{OR_2}{\|}}{\overset{S}{P}}-O-R_3 \quad (I)$$

| Compound No. | R₁ | R₂ | R₃ | Physical constant |
|---|---|---|---|---|
| 23 | CH₃OCH₂CH₂CH(CH₃) | C₂H₅ | O₂N-benzo[1,3]dioxol-5-yl | $n_D^{27.5}$ 1.5500 |
| 24 | CH₃OCH₂CH₂ | C₂H₅ | O₂N-benzo[1,3]dioxol-5-yl | $n_D^{24.5}$ 1.5639 |
| 25 | CH₃OCH₂CH(C₂H₅) | C₂H₅ | O₂N-benzo[1,3]dioxol-5-yl | M.P. 82–83° C. |
| 26 | CH₃O(CH₂)₃ | C₂H₅ | O₂N-benzo[1,3]dioxol-5-yl | $n_D^{24.5}$ 1.5588 |
| 27 | C₂H₅O(CH₂)₂ | C₂H₅ | O₂N-benzo[1,3]dioxol-5-yl | $n_D^{24.5}$ 1.5556 |
| 28 | C₂H₅O(CH₂)₃ | C₂H₅ | O₂N-benzo[1,3]dioxol-5-yl | $n_D^{24.5}$ 1.5512 |
| 29 | CH₃OCH₂CH(CH₃) | CH₃ | O₂N-benzo[1,3]dioxol-5-yl | $n_D^{21.5}$ 1.5581 |
| 30 | CH₃OCH₂CH₂CH(CH₃) | CH₃ | O₂N-benzo[1,3]dioxol-5-yl | $n_D^{21.5}$ 1.5372 |
| 31 | CH₂OCH₂CH(C₂H₅) | CH₃ | O₂N-benzo[1,3]dioxol-5-yl | $n_D^{25}$ 1.5505 |
| 32 | CH₃O(CH₂)₃ | CH₃ | O₂N-benzo[1,3]dioxol-5-yl | M.P. 63.5–66° C. |
| 33 | CH₃O(CH₂)₂ | CH₃ | O₂N-benzo[1,3]dioxol-5-yl | M.P. 76–79° C. |
| 34 | C₂H₅O(CH₂)₂ | CH₃ | O₂N-benzo[1,3]dioxol-5-yl | $n_D^{24}$ 1.5580 |
| 35 | C₂H₅O(CH₂)₃ | CH₃ | O₂N-benzo[1,3]dioxol-5-yl | $n_D^{24.5}$ 1.5531 |
| 36 | (CH₃O)₂CHCH₂ | C₂H₅ | O₂N-benzo[1,3]dioxol-5-yl | $n_D^{24.5}$ 1.5622 |
| 37 | (C₂H₅O)₂CHCH₂ | C₂H₅ | O₂N-benzo[1,3]dioxol-5-yl | $n_D^{24.5}$ 1.5350 |
| 38 | (CH₃OCH₂)₂CH | C₂H₅ | O₂N-benzo[1,3]dioxol-5-yl | $n_D^{25}$ 1.5445 |

TABLE 1-continued $$R_1NH-\underset{\underset{OR_2}{|}}{\overset{\overset{S}{\|}}{P}}-O-R_3 \quad (I)$$

| Compound No. | $R_1$ | $R_2$ | $R_3$ | Physical constant |
|---|---|---|---|---|
| 39 | (CH₃O)₂CHCH(CH₃) | C₂H₅ | 6-nitro-3,4-methylenedioxyphenyl | $n_D^{25}$ 1.5219 |
| 40 | NCCH₂CH₂ | C₂H₅ | 6-nitro-3,4-methylenedioxyphenyl | $n_D^{24.5}$ 1.5700 |
| 41 | FCH₂CH₂ | C₂H₅ | 6-nitro-3,4-methylenedioxyphenyl | $n_D^{24.5}$ 1.5654 |
| 42 | Br(CH₂)₃ | C₂H₅ | 6-nitro-3,4-methylenedioxyphenyl | $n_D^{24.5}$ 1.5820 |
| 43 | tetrahydrofuran-2-ylmethyl | C₂H₅ | 6-nitro-3,4-methylenedioxyphenyl | $n_D^{24.5}$ 1.5712 |
| 44 | CH₃SCH₂CH(CH₃) | C₂H₅ | 6-nitro-3,4-methylenedioxyphenyl | $n_D^{25}$ 1.5625 |
| 45 | NCCH(CH₃) | C₂H₅ | 6-nitro-3,4-methylenedioxyphenyl | Resinous |
| 46 | NCCH(CH₃) | CH₃ | 6-nitro-3,4-methylenedioxyphenyl | $n_D^{19.0}$ 1.5561 |
| 47 | tetrahydrothiopyran-4-yl | C₂H₅ | 6-nitro-3,4-methylenedioxyphenyl | Resinous |
| 48 | tetrahydropyran-4-yl | C₂H₅ | 6-nitro-3,4-methylenedioxyphenyl | $n_D^{23.0}$ 1.5702 |
| 49 | 1,1-dioxo-tetrahydrothiophen-3-yl | C₂H₅ | 6-nitro-3,4-methylenedioxyphenyl | M.P. 135–140° C. |
| 50 | ClCH₂CH₂ | C₂H₅ | 6-nitro-3,4-methylenedioxyphenyl | $n_D^{20.5}$ 1.5790 |
| 51 | BrCH₂CH₂ | C₂H₅ | 6-nitro-3,4-methylenedioxyphenyl | $n_D^{21.0}$ 1.5880 |
| 52 | 1-(thiophen-2-yl)ethyl | C₂H₅ | 6-nitro-3,4-methylenedioxyphenyl | $n_D^{21.5}$ 1.5968 |
| 53 | tetrahydrofuran-3-yl | C₂H₅ | 6-nitro-3,4-methylenedioxyphenyl | Resinous |
| 54 | tetrahydrothiophen-3-yl | C₂H₅ | 6-nitro-3,4-methylenedioxyphenyl | Resinous |

TABLE 1-continued

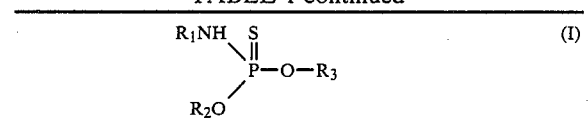

| Compound No. | R₁ | R₂ | R₃ | Physical constant |
|---|---|---|---|---|
| 55 | NCCH₂ | C₂H₅ | O₂N-[benzodioxole] | $n_D^{20.0}$ 1.5803 |
| 56 | cyclopropyl-CH(CH₃) | C₂H₅ | O₂N-[benzodioxole] | $n_D^{20.0}$ 1.5648 |
| 57 | tetrahydrothiopyran-4-yl | CH₃ | O₂N-[benzodioxole] | M.P. 110–112° C. |
| 58 | NCCH₂CH(CH₃) | CH₃ | O₂N-[benzodioxole] | $n_D^{19.0}$ 1.5561 |
| 59 | HC≡CCH₂S(CH₂)₂ | C₂H₅ | O₂N-[benzodioxole] | $n_D^{22.0}$ 1.5880 |
| 60 | CH₃S(CH₂)₂ | C₂H₅ | O₂N-[benzodioxole] | $n_D^{23.0}$ 1.5781 |
| 61 | CH₃ | CH₃ | 2,5-(OCH₃)₂-C₆H₃ | $n_D^{21}$ 1.5397 |
| 62 | C₂H₅ | CH₃ | 2,5-(OCH₃)₂-C₆H₃ | $n_D^{21.5}$ 1.5380 |

TABLE 1-continued

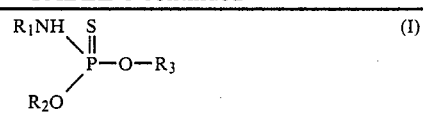

| Compound No. | R₁ | R₂ | R₃ | Physical constant |
|---|---|---|---|---|
| 63 | C₂H₅ | C₂H₅ | 2,5-(OCH₃)₂-C₆H₃ | $n_D^{21.5}$ 1.5334 |
| 64 | n-C₃H₇ | CH₃ | 2,5-(OCH₃)₂-C₆H₃ | $n_D^{21.5}$ 1.5284 |
| 65 | n-C₃H₇ | C₂H₇ | 2,5-(OCH₃)₂-C₆H₃ | $n_D^{21.5}$ 1.5320 |
| 66 | iso-C₃H₇ | CH₃ | 2,5-(OCH₃)₂-C₆H₃ | $n_D^{19.5}$ 1.5359 |
| 67 | iso-C₃H₇ | C₂H₅ | 2,5-(OCH₃)₂-C₆H₃ | $n_D^{21.0}$ 1.5269 |
| 68 | n-C₄H₉ | CH₃ | 2,5-(OCH₃)₂-C₆H₃ | $n_D^{20}$ 1.5291 |
| 69 | n-C₄H₉ | C₂H₅ | 2,5-(OCH₃)₂-C₆H₃ | $n_D^{20}$ 1.5244 |
| 70 | iso-C₄H₉ | CH₃ | 2,5-(OCH₃)₂-C₆H₃ | $n_D^{20}$ 1.5326 |

TABLE 1-continued $$\begin{array}{c} R_1NH \diagdown \overset{S}{\underset{\|}{P}} -O-R_3 \\ R_2O \diagup \end{array} \quad (I)$$

| Compound No. | R₁ | R₂ | R₃ | Physical constant |
|---|---|---|---|---|
| 71 | iso-C₄H₉ | C₂H₅ | 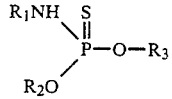 (2,4-di-OCH₃-phenyl) | $n_D^{20}$ 1.5271 |
| 72 | sec-C₄H₉ | CH₃ | 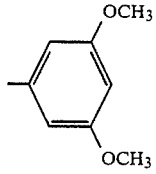 (2,4-di-OCH₃-phenyl) | $n_D^{19.0}$ 1.5329 |
| 73 | sec-C₄H₉ | C₂H₅ | 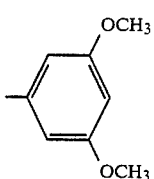 (2,4-di-OCH₃-phenyl) | $n_D^{23.5}$ 1.5262 |
| 74 | CH₃OCH₂CH(CH₃)— | C₂H₅ | 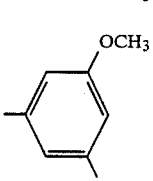 (2,4-di-OCH₃-phenyl) | $n_D^{23.5}$ 1.5300 |
| 75 | NCCH₂CH(CH₃)— | C₂H₅ | 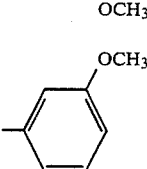 (2,4-di-OCH₃-phenyl) | $n_D^{24.5}$ 1.5368 |
| 76 | CH₃OCH₂CH(C₂H₅)— | C₂H₅ | 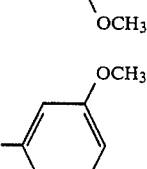 (2,4-di-OCH₃-phenyl) | $n_D^{23.5}$ 1.5260 |
| 77 | CH₃OCH₂CH(C₂H₅)— | CH₃ | 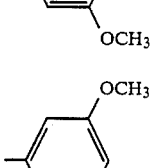 (2,4-di-OCH₃-phenyl) | $n_D^{25}$ 1.5215 |
| 78 | sec-C₄H₉ | C₂H₅ | 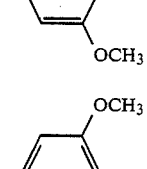 (3,4-methylenedioxyphenyl) | $n_D^{21.5}$ 1.5327 |
| 79 | NCCH₂CH(CH₃)— | C₂H₅ | 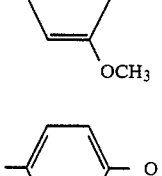 (3,4-methylenedioxyphenyl) | $n_D^{25.5}$ 1.5439 |
| 80 | iso-C₃H₇ | CH₃ | 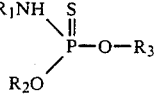 (3,4-methylenedioxyphenyl) | $n_D^{20.0}$ 1.5427 |
| 81 | iso-C₃H₇ | C₂H₅ | 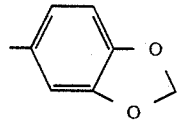 (3,4-methylenedioxyphenyl) | $n_D^{20.0}$ 1.5381 |

In actual application as fungicides, the phosphoramidothionates (I) may be used alone without incorporation of other ingredients such as carriers and diluents or, for easier application, in admixture with solid or liquid carriers. The fungicidal compositions can be formulated into any of ordinarily adopted forms such as, for example, dusts, granules, wettable powders, emulsifiable concentrates or flowables.

The fungicidal composition of the invention generally contains 0.1 to 99.9% by weight, preferably 2.0 to 80.0% by weight of the active ingredient.

As the solid carriers or diluents usable for formulation of the fungicidal composition, there may be exemplified plant carriers (e.g. wheat flour, tobacco powder, soybean powder, walnut-shell powder, wooden powder, saw dust, wheat bran, bark dust, cellulose powder, extract residue), fibrous products (e.g. paper, card board, rag), crushed synthetic resins, clays (e.g. kaoline, bentonite, terra alba), talcs, other inorganic minerals (e.g. pyrophyllite, celicite, pumice, sulfur powder, diatomaceous earth, white carbon, activated carbon), chemical fertilizers (e.g. ammonium sulfate, ammonium phosphate, ammonium nitrate, urea, ammonium chloride), etc. As the liquid carriers or diluents, there may be employed water, alcohols (e.g. methanol, ethanol), ketones (e.g. acetone, methylethylketone), ethers (e.g. diethyl ether, dioxane, cellosolve, tetrahydrofuran), aromatic hydrocarbons (e.g. benzene, toluene, xylene, methylnaphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, trichloroethylene, carbon tetrachloride), etc.

In addition to the solid or liquid carriers or diluents as exemplified above, there may be used surfactants when desired. Examples of the surfactants are polyoxyethylene phenylphenol polymer, polyoxyethylene alkylaryl ether, sodium laurylsulfate, calcium alkylbenzenesulfonate, alkylsulfates, alkylsulfonates, alkylarylsulfonates, polyethyleneglycol ethers, polyvalent alcohol esters, etc. There may be also used adhesive agents, dispersing agents, stabilizers, etc. Their specific examples are casein, gelatin, starch, carboxymethyl cellulose, gum arabic, alginate, calcium ligninsulfonate, bentonite, molasse, polyvinyl alcohol, palm oil, agar, isopropyl phosphate, tricresyl phosphate, tall oil, epoxylated oil, surfactants, aliphatic acids and their esters, etc.

Some typical examples of the fungicidal composition according to this invention are shown below. In those examples, part(s) and % are by weight unless otherwise indicated.

EXAMPLE A

Compound No. 1 (2 parts), clay (88 parts) and talc (10 parts) were thoroughly pulverized and mixed together to obtain a dust containing 2% of the active ingredient.

EXAMPLE B

Compound No. 25 (50 parts), synthetic silicon oxide hydrate (45 parts), a wetting agent (sodium laurylsulfate) (2 parts) and a dispersing agent (calcium ligninsulfonate) (3 parts) were thoroughly pulverized and mixed together to obtain a wettable powder containing 50% of the active ingredient.

EXAMPLE C

Compound No. 22 (10 parts), xylene (70 parts) and polyoxyethylene styrylphenyl ether (14 parts) and calcium dodecylbenzenesulfonate (6 parts) as emulsifiers were mixed together to obtain an emulsifiable concentrate containing 10% of the active ingredient.

EXAMPLE D

Compound No. 49 (2 parts), synthetic silicon oxide hydrate (1 part), a surfactant (calcium ligninsulfonate) (2 parts), bentonite (30 parts) and clay (65 parts) were mixed together while being powdered. The mixture was then kneaded with water, granulated and dried to obtain granules.

EXAMPLE E

Compound No. 71 (25 parts), polyoxyethylenesorbitan monooleate (3 parts), carboxymethyl cellulose (3 parts) and water (69 parts) were mixed together and pulverized until the particle size of the active ingredient becomes less than 5 microns to obtain flowables.

These compositions comprising the phosphoramidothionates (I) may be applied as such, or after diluted with water, to the plant in suitable application modes such as spraying, perfusion, dusting, etc. For instance, they may be applied to the plant for foliar treatment. Further, for instance, they may be spread over, perfused into or admixed with soil for soil treatment. If necessary, they may be used together with other fungicides to improve their activity as fungicides, and in some cases, a synergistic effect can be expected. They may be also applied in combination with insecticides, acaricides, nematocides, herbicides, plant growth regulators, fertilizers, soil improvers, etc.

A suitable amount of the fungicidal composition of the invention to be applied is generally from 0.5 to 500 grams, preferably 1 to 200 grams, in terms of the active ingredient per are. In case of the composition form such as wettable powder, emulsifiable concentrate or flowables, it is normally diluted with water before the application, and the concentration of the active ingredient is preferably within the range of 0.0005 to 0.5% by weight, preferably 0.001 to 0.2% by weight. In case of the composition form such as dust or granule, it is ordinarily applied as such.

The following examples show some typical test results supporting the excellent fungicidal activity of the phosphoramidothionates (I). In these examples, the compound numbers correspond to those in Table 1. The compounds used for comparison are as follows:

| Compound | Structure | Remarks |
| --- | --- | --- |
| A | Cl, CN, Cl, Cl, CN, Cl (tetrachloroisophthalonitrile) | Commercially available fungicide "Daconil" |
| B | CH$_2$—NH—CS—S—<br>CH$_2$—NH—CS—S—  Zn$^{2+}$ | Commercially available fungicide "Zineb" |
| C | CH$_2$—NH—CS—S—<br>CH$_2$—NH—CS—S—  Mn$^{2+}$ | Commercially available fungicide "Maneb" |

The fungicidal activities are expressed by the numerals 5, 4, 3, 2, 1 and 0, which represent the proportion of infected area on leaf and stem according to the following criteria:

| Fungicidal activity | State of infection |
| --- | --- |
| 5 | No infected area |
| 4 | Infected area of about 10% in the area of leaf and stem |
| 3 | Infected area of about 30% in the area of leaf and stem |
| 2 | Infected area of about 50% in the area of leaf and stem |
| 1 | Infected area of about 70% in the area of leaf and stem |
| 0 | Infected area of not less than 70% in the area of leaf and stem |

EXAMPLE I

Seeds of cucumber (species: "Sagamihanjiro") were sowed in soil filled in plastic pots and cultivated in a greenhouse for 14 days to obtain seedlings of cucumber having cotyledons. An aqueous dilution of the test compound in the form of emulsifiable concentrate was applied onto the seedlings by foliar treatment. Then, a spore suspension of Pseudoperonospora cubensis was sprayed onto the seedlings, which were placed at 20° C. under a humid condition for 3 days and grown at 20° C. under the irradiation with a fluorescent lamp for 3 days. The fungicidal activity was observed, of which the results are shown in Table 2.

TABLE 2

| Compound No. | Concentration of active ingredient (ppm) | Fungicidal activity |
| --- | --- | --- |
| 1 | 500 | 5 |
| 2 | 500 | 5 |
| 3 | 500 | 5 |
| 4 | 500 | 5 |
| 5 | 500 | 5 |
| 6 | 500 | 5 |
| 7 | 500 | 5 |
| 8 | 500 | 5 |
| 9 | 500 | 5 |
| 10 | 500 | 5 |
| 11 | 500 | 5 |
| 12 | 500 | 5 |

TABLE 2-continued

| Compound No. | Concentration of active ingredient (ppm) | Fungicidal activity |
|---|---|---|
| 13 | 500 | 5 |
| 14 | 500 | 5 |
| 15 | 500 | 5 |
| 16 | 500 | 5 |
| 17 | 500 | 5 |
| 18 | 500 | 5 |
| 19 | 500 | 5 |
| 20 | 500 | 5 |
| 21 | 500 | 5 |
| 22 | 500 | 5 |
| 23 | 500 | 5 |
| 24 | 500 | 5 |
| 25 | 500 | 5 |
| 26 | 500 | 5 |
| 27 | 500 | 5 |
| 28 | 500 | 5 |
| 29 | 500 | 5 |
| 30 | 500 | 5 |
| 31 | 500 | 5 |
| 32 | 500 | 5 |
| 33 | 500 | 5 |
| 34 | 500 | 5 |
| 35 | 500 | 5 |
| 36 | 500 | 5 |
| 37 | 500 | 5 |
| 38 | 500 | 5 |
| 39 | 500 | 5 |
| 40 | 500 | 5 |
| 41 | 500 | 5 |
| 42 | 500 | 5 |
| 43 | 500 | 5 |
| 44 | 500 | 5 |
| 45 | 500 | 5 |
| 46 | 500 | 5 |
| 47 | 500 | 5 |
| 48 | 500 | 5 |
| 49 | 500 | 5 |
| 50 | 500 | 5 |
| 51 | 500 | 5 |
| 52 | 500 | 5 |
| 53 | 500 | 5 |
| 54 | 500 | 5 |
| 55 | 500 | 5 |
| 56 | 500 | 5 |
| 57 | 500 | 5 |
| 58 | 500 | 5 |
| 59 | 500 | 5 |
| 60 | 500 | 5 |
| 61 | 500 | 5 |
| 62 | 500 | 5 |
| 63 | 500 | 5 |
| 64 | 500 | 5 |
| 65 | 500 | 5 |
| 66 | 500 | 5 |
| 67 | 500 | 5 |
| 68 | 500 | 5 |
| 69 | 500 | 5 |
| 70 | 500 | 5 |
| 71 | 500 | 5 |
| 72 | 500 | 5 |
| 73 | 500 | 5 |
| 74 | 500 | 5 |
| 75 | 500 | 5 |
| 76 | 500 | 5 |
| 77 | 500 | 5 |
| 78 | 500 | 5 |
| 79 | 500 | 5 |
| 80 | 500 | 5 |
| 81 | 500 | 5 |
| A | 500 | 0 |

EXAMPLE II

Seeds of cucumber (species: "Sagamihanjiro") were sowed in soil filled in plastic pots and cultivated in a greenhouse for 14 days to obtain seedlings of cucumber having cotyledons. A spore suspension of *Pseudoperonospora cubensis* was sprayed onto the seedlings, which were placed at 20° C. under a humid condition for 1 day. An aqueous dilution of the test compound in the form of emulsifiable concentrate was applied onto the seedlings by foliar treatment. Then, the plants were grown at 20° C. under irradiation with a fluorescent lamp for 4 days. The fungicidal activity was observed, of which the results are shown in Table 3.

TABLE 3

| Compound No. | Concentration of active ingredient (ppm) | Fungicidal activity |
|---|---|---|
| 1 | 200 | 5 |
| 2 | 200 | 5 |
| 3 | 200 | 5 |
| 6 | 200 | 5 |
| 7 | 200 | 5 |
| 9 | 200 | 5 |
| 10 | 200 | 5 |
| 11 | 200 | 5 |
| 12 | 200 | 5 |
| 16 | 200 | 5 |
| 17 | 200 | 5 |
| 19 | 200 | 5 |
| 20 | 200 | 5 |
| 21 | 200 | 5 |
| 22 | 200 | 5 |
| 23 | 200 | 5 |
| 24 | 200 | 5 |
| 25 | 200 | 5 |
| 26 | 200 | 5 |
| 29 | 200 | 5 |
| 31 | 200 | 5 |
| 32 | 200 | 5 |
| 38 | 200 | 5 |
| 40 | 200 | 5 |
| 41 | 200 | 5 |
| 42 | 200 | 5 |
| 43 | 200 | 5 |
| 44 | 200 | 5 |
| 45 | 200 | 5 |
| 46 | 200 | 5 |
| 45 | 200 | 5 |
| 46 | 200 | 5 |
| 47 | 200 | 5 |
| 48 | 200 | 5 |
| 50 | 200 | 5 |
| 51 | 200 | 5 |
| 54 | 200 | 5 |
| 55 | 200 | 5 |
| 57 | 200 | 5 |
| 58 | 200 | 5 |
| 60 | 200 | 5 |
| 64 | 200 | 5 |
| 65 | 200 | 5 |
| 66 | 200 | 5 |
| 68 | 200 | 5 |
| 69 | 200 | 5 |
| 72 | 200 | 5 |
| 74 | 200 | 5 |
| 75 | 200 | 5 |
| 77 | 200 | 5 |
| 79 | 200 | 5 |
| 80 | 200 | 5 |
| 81 | 200 | 5 |
| A | 200 | 0 |

EXAMPLE III

Seeds of cucumber (species: "Sagamihanjiro") were sowed in soil filled in plastic pots and cultivated in a greenhouse for 14 days to obtain seedlings of cucumber having cotyledons. The seedlings were treated by soil-drench with an aqueous dilution of the test compound in the form of emulsifiable concentrate. After 6 days, a spore suspension of *Pseudoperonospora cubensis* was sprayed onto the seedlings, which were placed at 20° C. under a humid condition for 1 day and then grown at 20° C. under the irradiation with a fluorescent lamp for 5 days. The fungicidal activity was observed, of which the results are shown in Table 4.

TABLE 4

| Compound No. | Amount of active ingredient (g/are) | Fungicidal activity |
| --- | --- | --- |
| 3 | 200 | 5 |
| 5 | 200 | 5 |
| 10 | 200 | 5 |
| 12 | 200 | 5 |
| 13 | 200 | 5 |
| 16 | 200 | 5 |
| 18 | 200 | 5 |
| 20 | 200 | 5 |
| 22 | 200 | 5 |
| 23 | 200 | 5 |
| 24 | 200 | 5 |
| 26 | 200 | 5 |
| 27 | 200 | 5 |
| 29 | 200 | 5 |
| 30 | 200 | 5 |
| 31 | 200 | 5 |
| 32 | 200 | 5 |
| 33 | 200 | 5 |
| 38 | 200 | 5 |
| 39 | 200 | 5 |
| 41 | 200 | 5 |
| 46 | 200 | 5 |
| 50 | 200 | 5 |
| 55 | 200 | 5 |
| 59 | 200 | 5 |
| A | 500 | 0 |

EXAMPLE IV

Seeds of grape (species: "Neomus") were sowed in soil filled in plastic pots and cultivated in a greenhouse for 50 days to obtain seedlings of grape at the 2 to 3-leaved stage. A spore suspension of *Plasmopara viticola* was sprayed onto the seedlings, which were placed at 23° C. under a humid condition for 1 day. Then, an aqueous dilution of the test compound in the form of emulsifiable concentrate was applied onto the seedlings by foliar treatment. Thereafter, the seedlings were grown at 23° C. under the irradiation with a fluorescent lamp for 14 days. The fungicidal activity was observed, of which the results are shown in Table 5.

TABLE 5

| Compound No. | Concentration of active ingredient (ppm) | Fungicidal activity |
| --- | --- | --- |
| 1 | 500 | 5 |
| 2 | 500 | 5 |
| 3 | 500 | 5 |
| 6 | 500 | 5 |
| 7 | 500 | 5 |
| 9 | 500 | 5 |
| 10 | 500 | 5 |
| 11 | 500 | 5 |
| 12 | 500 | 5 |
| 13 | 500 | 5 |
| 16 | 500 | 5 |
| 22 | 500 | 5 |
| 23 | 500 | 5 |
| 24 | 500 | 5 |
| 25 | 500 | 5 |
| 26 | 500 | 5 |
| 28 | 500 | 5 |
| 29 | 500 | 5 |
| 30 | 500 | 5 |
| 31 | 500 | 5 |
| 32 | 500 | 5 |
| 33 | 500 | 5 |
| 36 | 500 | 5 |
| 38 | 500 | 5 |
| 39 | 500 | 5 |
| 40 | 500 | 5 |
| 41 | 500 | 5 |
| 43 | 500 | 5 |
| 44 | 500 | 5 |
| 45 | 500 | 5 |
| 46 | 500 | 5 |
| 47 | 500 | 5 |
| 48 | 500 | 5 |
| 50 | 500 | 5 |
| 51 | 500 | 5 |
| 53 | 500 | 5 |
| 54 | 500 | 5 |
| 56 | 500 | 5 |
| 57 | 500 | 5 |
| 58 | 500 | 5 |
| 59 | 500 | 5 |
| 60 | 500 | 5 |
| 62 | 500 | 5 |
| 63 | 500 | 5 |
| 64 | 500 | 5 |
| 65 | 500 | 5 |
| 66 | 500 | 5 |
| 68 | 500 | 5 |
| 69 | 500 | 5 |
| 70 | 500 | 5 |
| 72 | 500 | 5 |
| 73 | 500 | 5 |
| 74 | 500 | 5 |
| 75 | 500 | 5 |
| 81 | 500 | 5 |
| B | 1000 | 0 |

EXAMPLE V

Seeds of potato (species: "Danshaku") were sowed in soil filled in plastic pots and cultivated in a greenhouse for 2 months to obtain seedlings of potato. A spore suspension of *Phytophthora infestans* were sprayed onto the seedlings, which were placed at 20° C. under a humid condition for 1 day. Then, an aqueous dilution of the test compound in the form of emulsifiable concentrate was applied onto the seedlings by foliar treatment. Thereafter, the seedlings were grown at 20° C. under a humid condition for 6 days. The fungicidal activity was observed, of which the results are shown in Table 6.

TABLE 6

| Compound No. | Concentration of active ingredient (ppm) | Fungicidal activity |
| --- | --- | --- |
| 1 | 500 | 5 |
| 2 | 500 | 5 |
| 7 | 500 | 5 |
| 11 | 500 | 5 |
| 12 | 500 | 5 |
| 22 | 500 | 5 |
| 23 | 500 | 5 |
| 25 | 500 | 5 |
| 29 | 500 | 5 |
| 30 | 500 | 5 |
| 31 | 500 | 5 |
| 38 | 500 | 5 |
| 42 | 500 | 5 |
| 45 | 500 | 5 |
| 46 | 500 | 5 |
| 47 | 500 | 5 |
| 48 | 500 | 5 |
| 53 | 500 | 5 |
| 54 | 500 | 4 |
| 57 | 500 | 4 |
| 58 | 500 | 4 |
| 64 | 500 | 4 |
| 65 | 500 | 3 |
| 66 | 500 | 3 |
| 68 | 500 | 5 |
| 69 | 500 | 5 |
| 70 | 500 | 4 |
| 73 | 500 | 4 |

TABLE 6-continued

| Compound No. | Concentration of active ingredient (ppm) | Fungicidal activity |
| --- | --- | --- |
| 74 | 500 | 4 |
| 75 | 500 | 4 |
| 80 | 500 | 3 |
| C | 1000 | 0 |

What is claimed is:

1. A phosphoramidothionate of the formula:

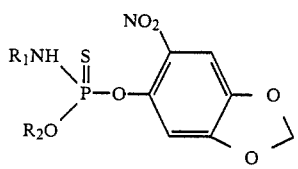

wherein $R_1$ is a hydrogen atom, a lower alkyl group, a lower alkenyl group, a lower alkynyl group, a lower cycloalkyl group, a lower cycloalkyl(lower)alkyl group, a halo(lower)alkyl group, a lower alkoxy(lower)alkyl group, a di(lower)alkoxy(lower)alkyl group, a cyano(lower)alkyl group, a lower alkylthio(lower)alkyl group, a lower alkynylthio(lower)alkyl group, a lower dioxothiacycloalkyl group, a lower thiacycloalkyl group, a lower oxacycloalkyl group, a lower oxacycloalkyl(lower)alkyl group or a thienyl(lower)alkyl group and $R_2$ is a lower alkyl group.

2. The phosphoramidothionate according to claim 1, wherein $R_1$ is a hydrogen atom, a $C_1$-$C_5$ alkyl group, a $C_3$-$C_4$ alkenyl group, a $C_3$ alkynyl group, a $C_3$-$C_6$ cycloalkyl group, a $C_3$ cycloalkyl($C_2$)alkyl group, a halo($C_2$-$C_3$)alkyl group, a $C_1$-$C_2$ alkoxy($C_2$-$C_4$)alkyl group, a di($C_1$-$C_2$)alkoxy($C_2$)alkyl group, a cyano($C_1$-$C_3$)alkyl group, a $C_1$ alkylthio($C_3$)alkyl group, a $C_3$ alkynylthio($C_2$)alkyl group, a 1,1-dioxotetrahydrothien-3-yl group, a tetrahydrothiopyran-4-yl group, a tetrahydropyran-4-yl group, a tetrahydrofurfuryl group, a tetrahydrofuryl group, a tetrahydrothienyl group or a 1-(thienyl)ethyl group and $R_2$ is a $C_1$-$C_2$ alkyl group.

3. The phosphoramidothionate according to claim 1, wherein $R_1$ is a hydrogen atom.

4. The phosphoramidothionate according to claim 1, wherein $R_1$ is a lower alkyl group.

5. The phosphoramidothionate according to claim 1, wherein $R_1$ is a lower cycloalkyl group.

6. The phosphoramidothionate according to claim 1, wherein $R_1$ is represented by the formula:

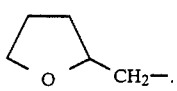

7. The phosphoramidothionate according to claim 2, wherein $R_1$ is represented by the formula:

8. The phosphoramidothionate according to claim 2, wherein $R_2$ is an ethyl group.

9. The phosphoramidothionate according to claim 2, wherein $R_1$ is represented by the formula:

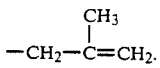

10. The phosphoramidothionate according to claim 2, wherein $R_1$ is represented by the formula:

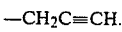

11. The phosphoramidothionate according to claim 2, wherein $R_1$ is represented by the formula:

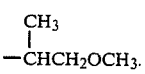

12. The phosphoramidothionate according to claim 2, wherein $R_1$ is represented by the formula:

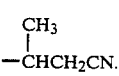

13. The phosphoramidothionate according to claim 2, wherein $R_1$ is represented by the formula:

14. A phosphoramidothionate of the formula:

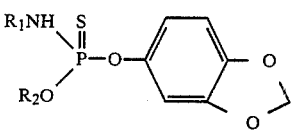

wherein $R_1$ is a hydrogen atom, a lower alkyl group, a lower alkenyl group, a lower alkynyl group, a lower cycloalkyl group, a lower cycloalkyl(lower)alkyl group, a halo(lower)alkyl group, a lower alkoxy(lower)alkyl group, a di(lower)alkoxy(lower)alkyl group, a cyano(lower)alkyl group, a lower alkylthio(lower)alkyl group, a lower alkynylthio(lower)alkyl group, a lower dioxothiacycloalkyl group, a lower thiacycloalkyl group, a lower oxacycloalkyl group, a lower oxacycloalkyl(lower)alkyl group or a thienyl(lower)alkyl group and $R_2$ is a lower alkyl group.

15. The phosphoramidothionate according to claim 14, whererin $R_1$ is a hydrogen atom, a $C_1$-$C_5$ alkyl group, a $C_3$-$C_4$ alkenyl group, a $C_3$ alkynyl group, a $C_3$-$C_6$ cycloalkyl group, a $C_3$ cycloalkyl($C_2$)alkyl group, a halo($C_2$-$C_3$)alkyl group, a $C_1$-$C_2$ alkoxy($C_2$-$C_4$)alkyl group, a di($C_1$-$C_2$)alkoxy($C_2$)alkyl group, a cyano($C_1$-$C_3$)alkyl group, a $C_1$ alkylthio($C_3$)alkyl group, a $C_3$ alkynylthio($C_2$)alkyl group, a 1,1-dioxotetrahydrothien-3-yl group, a tetrahydrothiopyran-4-yl group, a tetrahydropyran-4-yl group, a tetrahydrofurfuryl group, a tetrahydrofuryl group, a tetrahydrothienyl group or a 1-(thienyl)ethyl group and $R_2$ is a $C_1$-$C_2$ alkyl group.

16. The phosphoramidothionate according to claim 14, wherein $R_1$ is a hydrogen atom.

17. The phosphoramidothionate according to claim 14, wherein $R_1$ is a lower alkyl group.

18. The phosphoramidothionate according to claim 14, wherein $R_1$ is a lower cycloalkyl group.

19. The phosphoramidothionate according to claim 15, wherein $R_1$ is a propyl group.

20. The phosphoramidothionate according to claim 15, wherein $R_2$ is either methyl or ethyl.

21. A fungicidal composition which comprises as an active ingredient a fungicidally effective amount of the compound according to claim 8 and an inert carrier or diluent.

22. A fungicidal composition which comprises as an active ingredient a fungicidally effective amount of the compound according to claim 14 and an inert carrier or diluent.

23. A method for controlling fungi which comprises applying a fungicidally effective amount of the phosphoramidothionate according to claim 1 to phytopathogenic fungi.

24. A method for controlling fungi which comprises applying a fungicidally effective amount of the phosphoramidothionate according to claim 14 to phytopathogenic fungi.

* * * * *